US005657765A

United States Patent [19]

Est

[11] Patent Number: 5,657,765

[45] Date of Patent: Aug. 19, 1997

[54] EROTIC STIMULATOR

[76] Inventor: Steven S. Est, 810 Nancyrose St., Houston, Tex. 77015

[21] Appl. No.: 571,754

[22] Filed: Dec. 13, 1995

[51] Int. Cl.[6] .................... A61F 6/02; A61C 5/14

[52] U.S. Cl. .................... 128/842; 128/861

[58] Field of Search .................... 128/848, 858–862, 128/842, 844; 2/2

[56] References Cited

U.S. PATENT DOCUMENTS

| | | | |
|---|---|---|---|
| D. 357,323 | 4/1995 | Leonard | D24/215 |
| 3,626,931 | 12/1971 | Bysakh | 600/38 |
| 3,996,930 | 12/1976 | Sekulich | 600/38 |
| 4,002,164 | 1/1977 | Bradley | 601/135 |
| 4,852,586 | 8/1989 | Haines | 128/844 |
| 4,919,149 | 4/1990 | Stang | 128/844 |
| 4,949,731 | 8/1990 | Harding | 128/842 |
| 5,318,043 | 6/1994 | Burr | 128/844 |
| 5,465,734 | 11/1995 | Alvarez | 128/860 |

*Primary Examiner*—Michael A. Brown
*Attorney, Agent, or Firm*—Robbins & Robbins

[57] ABSTRACT

An erotic stimulator in the form of a tongue is provided. The stimulator comprises a flexible, elongated member having a mouthpiece at its base end whereby a user can manipulate the stimulator while leaving the hands free during gynecological stimulation with the device. The device has a plurality of raised projections on its surface to provide enhanced stimulation to the more sensitive areas of the female anatomy.

8 Claims, 3 Drawing Sheets

EROTIC STIMULATOR

BACKGROUND OF THE INVENTION

There exist a number of devices for enhancing the sexual experience among couples. The demand for such products is indisputable, and this fact is supported by the vast growth of sales of such products and the acceptability by marriage counselors, physicians, planned parent groups and the like for their use as an adjunct to a healthy and meaningful relationship, both sexually and spiritually. Such devices also provide a satisfactory alternative to actual penile intercourse in certain instances where it is either not possible, in the case of impotency, or not desirable in the event pregnancy is to be avoided.

Many sexual aid devices are phallic in design and provide a source of enhanced stimulation to the female partner. Massagers are a popular tool, and range from plain elongated pieces of plastic to fancier vibrating models. There is the desire on the part of many to give a certain air of excitement and fun to such devices, as well. Toward this end, many massager devices incorporate a realistic look, approximating the actual look, feel and dimensions of an actual penis.

SUMMARY OF THE INVENTION

The erotic stimulator of the instant invention is designed to provide enhanced stimulation to the female sexual partner and provides an alternative to actual penile intercourse. The stimulator comprises a flexible, elongated member in the form of an enlarged tongue, which has means at its base end by which a user can hold and manipulate through engagement with the mouth, just as if it were an extension of the tongue. The elongated tongue member has a plurality of raised projections on its surface which, when come into contact with certain sensitive areas of the female vagina and clitoris, provide an enhanced stimulative effect.

The mouthpiece is formed of pliable plastic to enable the user to bear down and form a solid, yet comfortable, grip on the device so that he may manipulate the device as desired.

It is therefore an object of this invention to provide an erotic stimulator for providing enhanced stimulation to the female during sexual activity.

The above features are objects of this invention. Further objects will appear in the detailed description which follows and will be otherwise apparent to those skilled in the art.

For purpose of illustration of this invention a preferred embodiment is shown and described hereinbelow in the accompanying drawing. It is to be understood that this is for the purpose of example only and that the invention is not limited thereto.

IN THE DRAWINGS

DESCRIPTION OF THE INVENTION

Figure 1:
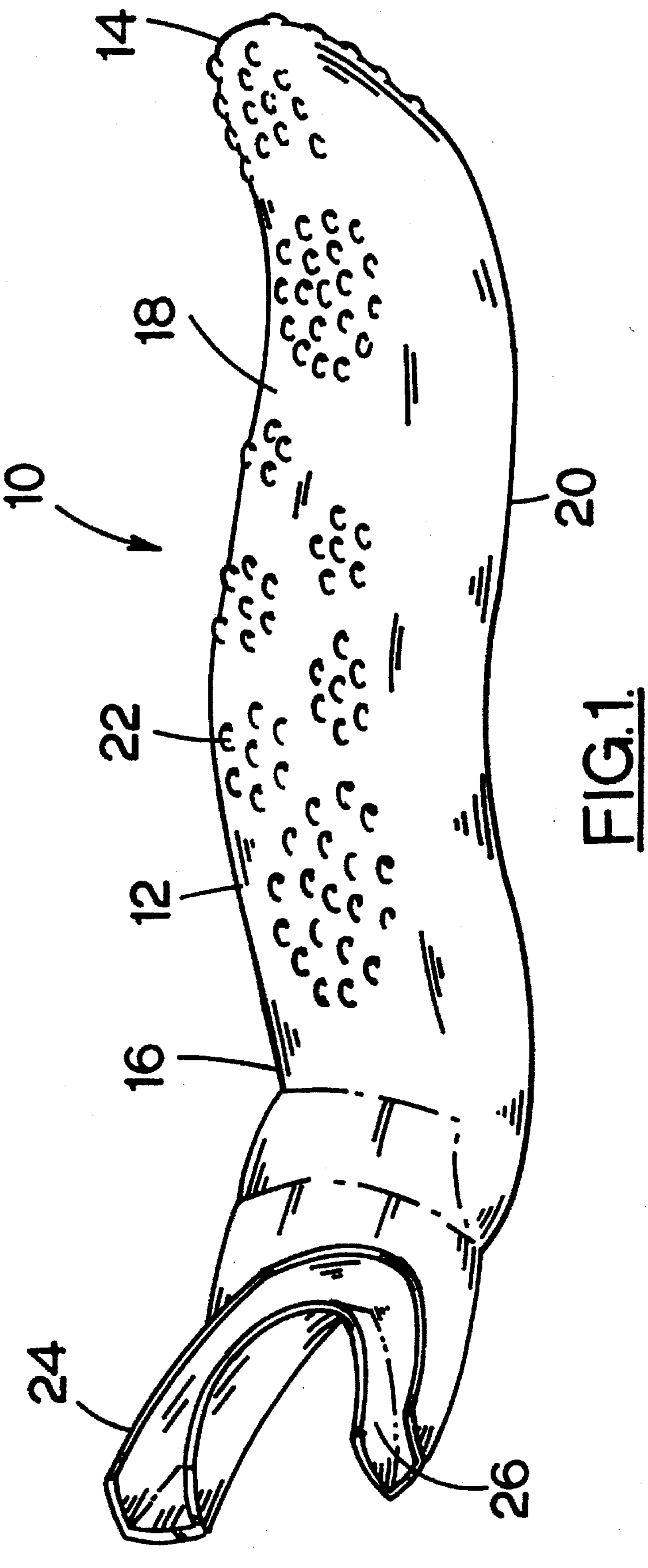
FIG. 1 is a perspective view of the erotic stimulator.
Figure 2:
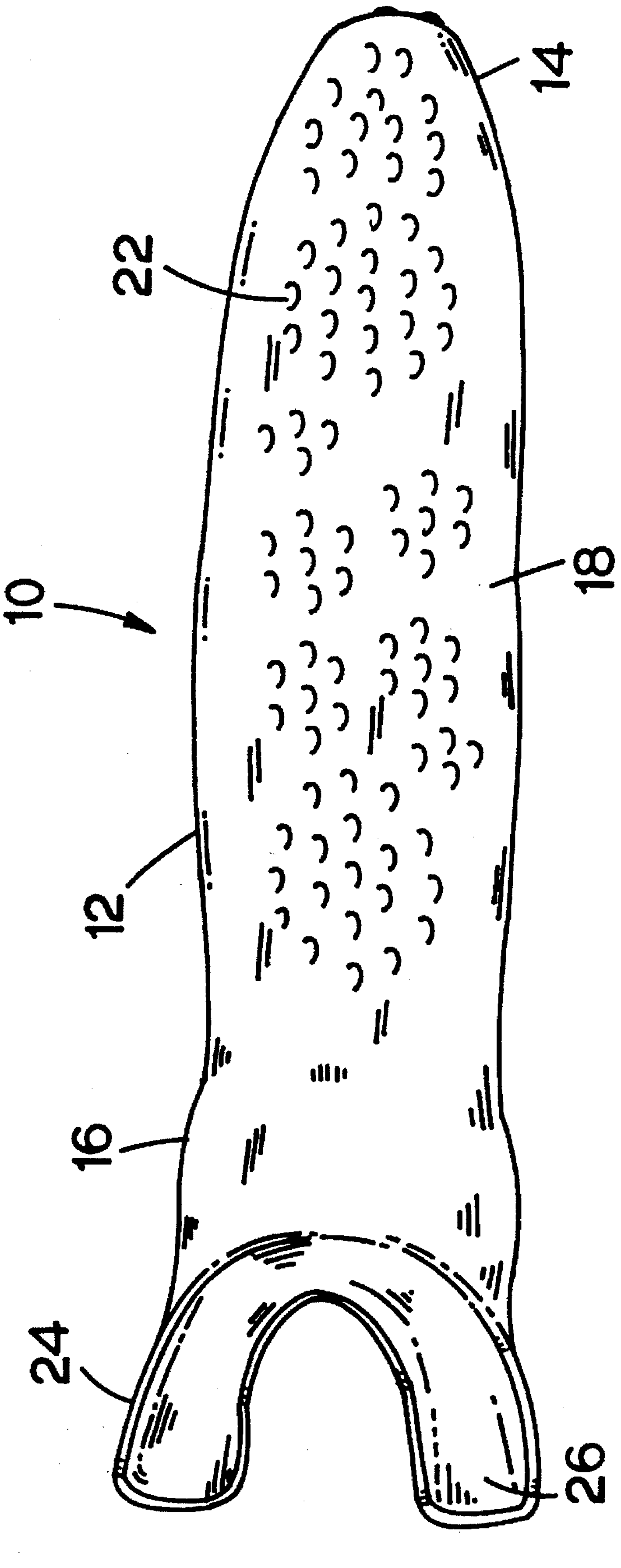
FIG. 2 is a top plan view.
Figure 3:
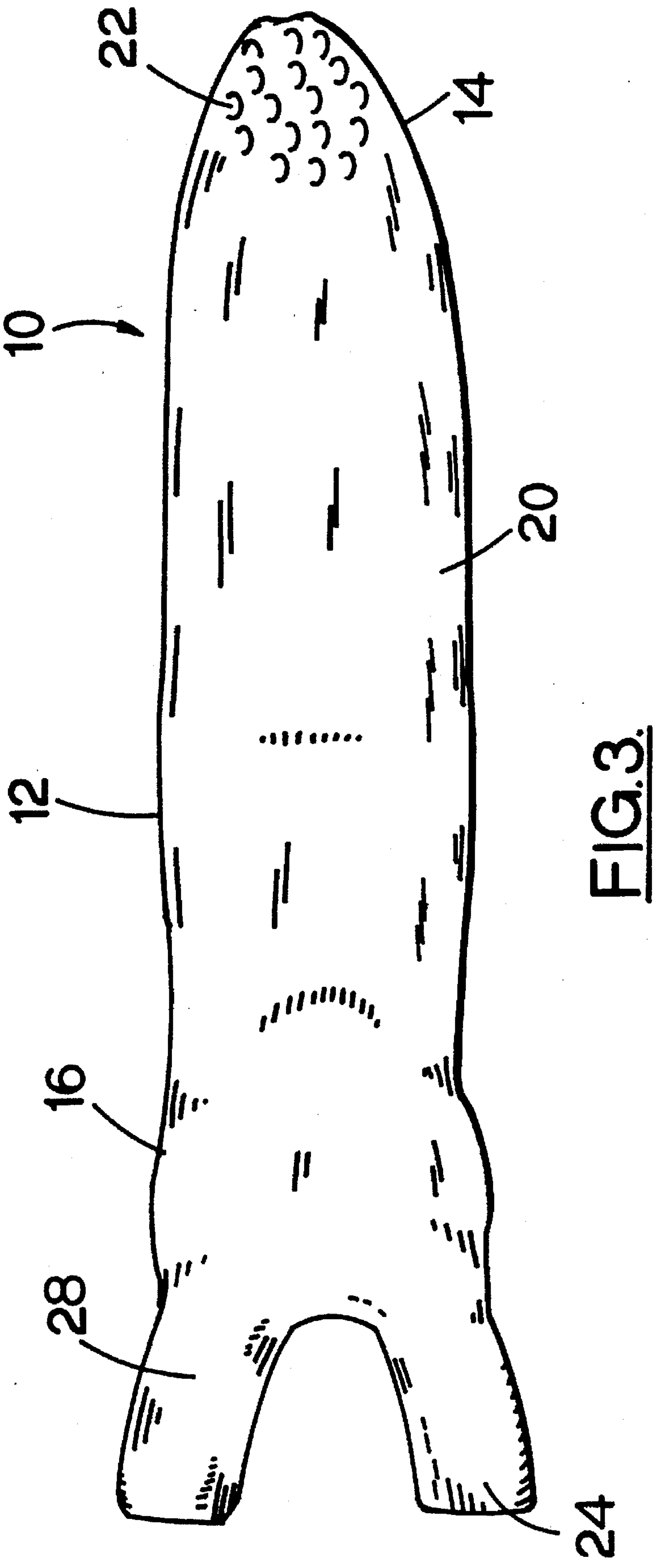
FIG. 3 is a bottom plan view.

The erotic stimulator of the instant invention is generally indicated by the reference numeral 10 as shown in FIG. 1. It is comprised of a flexible, elongated member 12 which may be made of neoprene rubber or other suitable material. Because this device may be used with lubricants, the material should be resistent to oil and other chemicals. Elongated member 12 has a tip end 14, base end 16, top surface 18 and bottom surface 20. Member 12 may be planar, or it may be preformed so as to be curved and undulating in shape as shown in FIG. 1. The resiliency and pliancy of the material allows member 12 to be bent and twisted during use. The size of different models of member 12 can be varied as custom of usage dictates, with the average size falling within the range of three to nine inches.

Raised projections 22 are disposed along top surface 18 and bottom surface 20. They can vary in size and average around 1/16 of an inch in height. The placement of and distance between discrete projections 22 can be varied, and can be placed in distinct groupings, or scattered over the entire surface.

A mouthpiece 24 is integrally attached to base end 16. It allows a user to manipulate the device by mouth while leaving the hands free during activity with a partner. Mouthpiece 24 comprises a walled arcuate trough 26 which receives the upper teeth of the user. The bottom surface 28 of the mouthpiece is pliable and provides a substrate against which the lower teeth can firmly engage to help maintain a steady grip on the device during use. Other shaped mouthpieces can also be used, such as a solid U-shaped, or even planar, piece, which can allow the user to invert the device so that the aspect of the tongue of the device is essentially upside down in relation to the user's mouth during use. The mouthpiece feature provides a distinct advantage over other devices, such as those using a headstrap or the like, in that the user can quickly and easily engage and disengage the device of the instant invention.

The erotic stimulator of the present invention thus provides a simple, yet effective device for providing enhanced stimulation to the female partner and serves as a useful adjunct for sexual activity. To add to the attractiveness or appeal of the device, it could be colored in pleasing tones if so desired.

Various changes and modifications may be made within this invention as will be apparent to those skilled in the art. Such changes and modifications are within the scope and teaching of this invention as defined in the claims appended hereto.

What is claimed is:

1. An erotic stimulator comprising a flexible, non-hollow and semi-rigid, elongated member, said member having a tip end and a base end and having a length greater than 3 inches, said base end having means for engagement with a user's mouth such that said member extends externally from said mouth.

2. The erotic stimulator of claim 1 in which said member comprises the shape of an extended tongue.

3. The erotic stimulator of claim 2 in which said member has a plurality of raised projections on a top surface thereof.

4. The erotic stimulator of claim 2 in which said member has a plurality of raised projections on a bottom surface thereof.

5. The erotic stimulator of claim 4 in which said raised projections are disposed on an underneath side of said tip end.

6. The erotic stimulator of claim 2 in which said member is preformed, having an undulate shape.

7. An erotic stimulator comprising a flexible non-hollow and semi-rigid, elongated member, said member having a tip end and a base end, and having a length greater than 3 inches said base end having means for engagement with a user's mouth, a mouthpiece being integrally attached to said base end, said mouthpiece having an arcuate trough for receiving the upper teeth of a user, whereby a user manipulates said stimulator with said user's mouth.

8. An erotic stimulator comprising a flexible, elongated member, said member having a tip end and a base end, said base end having means for engagement with a user's mouth, said member comprising the shape of a tongue, a surface of said member having a plurality of raised projections thereon, said member being preformed and having an undulate shape, a mouthpiece being integrally attached to said base end, said mouthpiece having an arcuate trough for receiving the upper teeth of a user, whereby a user manipulates said stimulator with said user's mouth.

* * * * *